US00PP11467P

United States Patent [19]

Lemon

[11] Patent Number: Plant 11,467

[45] Date of Patent: Aug. 1, 2000

[54] VARIETY OF GERANIUM NAMED 'FIREBALL'

[75] Inventor: David Lemon, Lompoc, Calif.

[73] Assignee: Oglevee, Ltd., Connellsville, Pa.

[21] Appl. No.: 09/103,185

[22] Filed: Jun. 24, 1998

[51] Int. Cl.[7] ..... A01H 5/00

[52] U.S. Cl. ..... Plt./330

[58] Field of Search ..... Plt./330

*Primary Examiner*—Howard J. Locker
*Assistant Examiner*—Anne Marie Grünberg
*Attorney, Agent, or Firm*—Webb Ziesenheim Logsdon Orkin & Hanson, P.C.

[57] ABSTRACT

The new cultivar maintains a controlled growth habit allowing for tight growing. It is very tolerant to heat at low humidity and to cool temperatures at high humidity. The bloom color is a bright intense red on a dark green foliage.

1 Drawing Sheet

BACKGROUND OF THE INVENTION

The present invention comprises a new and distinct cultivar of *Pelargonium×hortorum* known by the varietal name 'Fireball' (Oglevee No. 5084, Breeder No. 4DG872). The new variety was discovered in a selected breeding program in Lompoc, Calif. as a cross between 'Tango' (U.S. Plant Pat. No. 5,933) and 'Victoria' (U.S. Plant Pat. No. 6,064). The new variety was first asexually reproduced by cuttings at Oglevee, Ltd. in Connellsville, Pa. on Feb. 22, 1995. The new variety has been asexually reproduced by cuttings at Oglevee, Ltd. in Connellsville, Pa. over a several year period. It has also been trial and field tested at Connellsville and has been found to retain its distinctive characteristics through successive propagations.

The cultivar, when grown in a glass greenhouse in Connellsville, Pa. using natural light and temperatures of 60° F. night and 68° F. day, has a response time of six weeks from a rooted cutting to flowering in a 10 cm pot. The response time was determined on plants grown in soilless media employing constant fertilizer 200–250 parts per million of nitrogen and potassium in full light.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. The plant history was taken on six week plants blossomed under natural light in a greenhouse and the color readings were taken on a plant grown in a 20 cm pot on Feb. 24, 1998 indoors under 200–220 foot candles of fluorescent cool white light. Color references are primarily to The R.H.S. Colour Chart of The Royal Horticultural Society of London.

PLANT

Classification:
- *Botanical.*—*Pelargonium×hortorum.*
- *Commercial.*—Zonal florist's geranium.

Form: Medium mound habit.
- *Height.*—19–23 cm above top of pot.
- *Growth.*—Free basal branching.

Strength: Does not require artificial support.

Foliage: Stalked leaf attachment; dark green with slight zone present; slightly reflective.

Leaves:
- *Size.*—6.5–8.5 cm across at the widest point.
- *Shape.*—Reniform; cordate base.
- *Margin.*—Crenate.
- *Texture.*—Pubescent.
- *Color.*—Top: Green Group 139A. Bottom: Yellow-Green Group 147B.
- *Ribs and veins.*—Venation: Palmate. Color: Yellow-Green Group 146B.
- *Zone color.*—Brown Group 200A, may not be noticeable.

Petioles:
- *Color.*—Yellow-Green Group 146B.
- *Length.*—5.4–6.1 cm.

Stem:
- *Color.*—Yellow-Green Group 146B.
- *Internode length.*—1.0–2.0 cm.

THE BUD

Shape: Oval cluster.

Size: 2.0–2.5 cm across bud cluster at the widest point; buds not showing any color.

Time of bud burst: 4–5 weeks after planting.

INFLORESCENCE

Blooming habit: Continuous; free and early flowering; flowers last up to 14 days.

Size:
- *Closed florets.*—0.9–1.2 cm long; 0.6–0.8 cm wide; bud just beginning to show color.
- *Fully opened bloom.*—9.0–10.5 cm across.

Borne: Floret on pedicel; pedicel on peduncle; 5.0–10.0 cm above foliage.

Shape of umbel: Semispherical.

Florets:
- *Form.*—Flat to slightly cupped; 5.0–5.4 cm across at the widest point.
- *Number per umbel.*—16–28.
- *Color.*—Top: Red Group 44A. Bottom: Red Group 44C. Eye: Present on all true petals although may not be seen from a distance; varies in size and color from one petal to another; lighter eye: Red-Purple Group 60C, darker eye: Red-Purple Group 60A.
- *Petals.*—7–10 in number; 2.6–3.1 cm long; 2.3–2.5 cm wide.

*Texture and appearance.*—Appearance from a distance is a rich clear red above dark green foliage.

Petaloids:

*Quantity.*—6–8.

*Shape.*—Some petal-like with pollen attached, others flat but twisted; some tubular.

*Color.*—Top: Red Group 44B. Bottom: Red Group 44C.

Pedicel:

*Length.*—3.0–3.6 cm.

*Color.*—Yellow-Green Group 146C at the base with an overlay of Greyed-Purple Group 183B.

Peduncle:

*Length.*—9.7–16.5 cm.

*Color.*—Yellow-Green Group 146C at the base with an overlay of Greyed-Purple Group 183B mid-way up the peduncle.

Disease resistance: Not known.

REPRODUCTIVE ORGANS

Stamens:

*Anthers.*—3–4 mm long.

*Filaments.*—No true filaments present; pollen is attached to petaloids.

*Pollen.*—Orange-Red Group 34B.

Pistils:

*Number.*—1.

*Length.*—1.0–1.1 cm.

*Stigma.*—5–6 parted; Red-Purple Group 59B.

*Style.*—3–4 mm long.

Ovaries: Superior; Yellow-Green Group 146C; 6–7 mm long.

Fruit: None observed.

GENERAL CHARACTERISTICS

'Fireball' was selected as a replacement for the current variety of 'Red Hots' (U.S. Plant Pat. No. 9,305). The variety was tested over a three-year period against 'Red Hots' and also 'Tango' (U.S Plant Pat. No. 5,933). It was found to be superior to both in greenhouse and outdoor garden trials withstanding either high temperature and low moisture or low temperature and high moisture. Indoors it was at least 7 days earlier than 'Tango' and did not show petal burning which is very prevalent in 'Red Hots'. Its neat plant habit allows for tighter growing. Cutting production is equal to that of 'Red Hots' and better than 'Tango'. Rooting speed is very acceptable at 21 days. 'Fireball' finishes as a neat medium mound of dark green foliage with a burst of bright intense red flowers.

I claim:

1. A new and distinct variety of geranium plant substantially as shown and described.

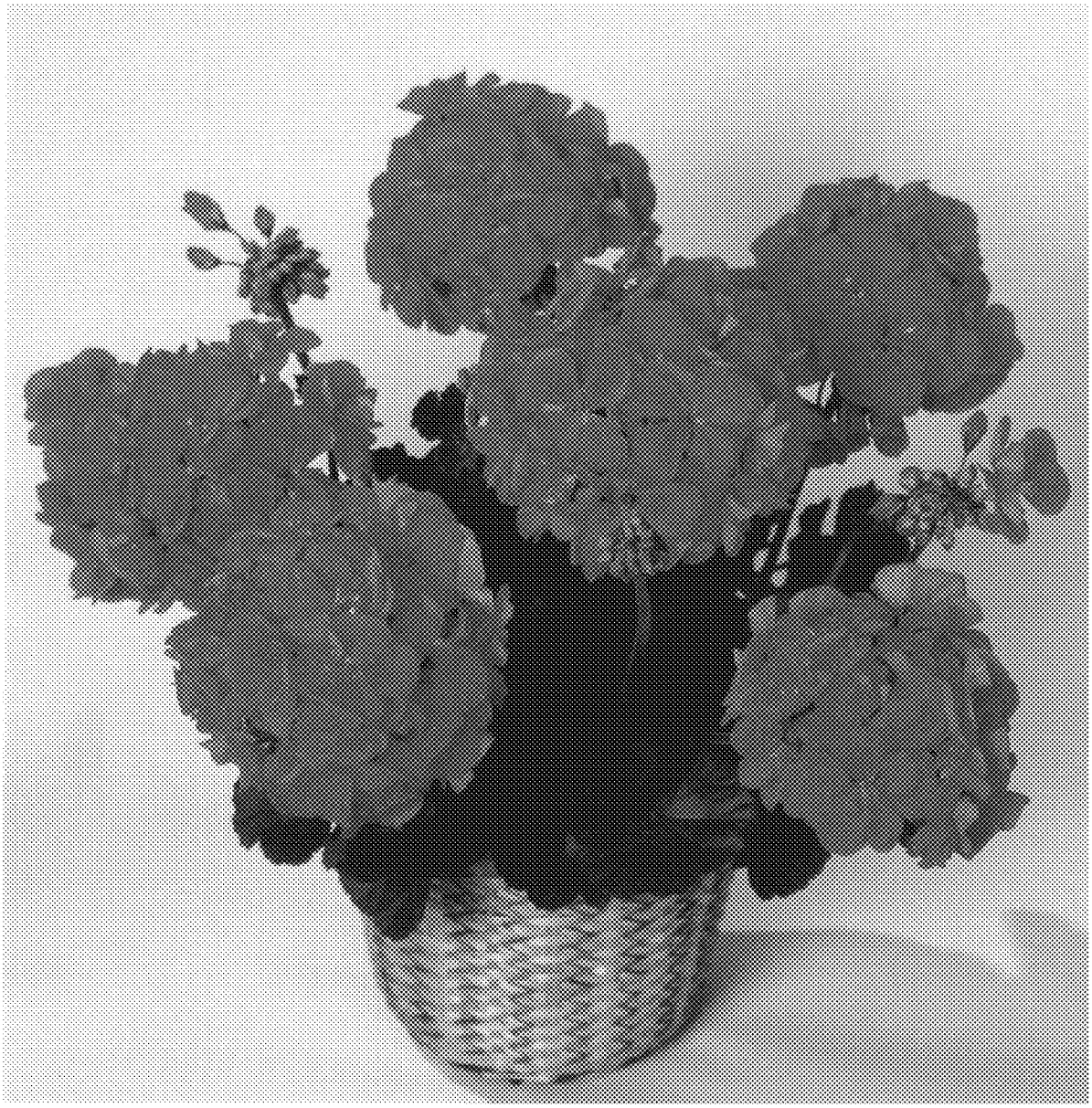

* * * * *